(12) United States Patent
Echols et al.

(10) Patent No.: US 11,266,368 B2
(45) Date of Patent: Mar. 8, 2022

(54) RADIOGRAPH DENSITY DETECTION DEVICE

(71) Applicant: Scarlet Imaging Radiology, LLC, Salt Lake City, UT (US)

(72) Inventors: Michael Scott Echols, Salt Lake City, UT (US); Edward Hsu, Salt Lake City, UT (US)

(73) Assignee: SCARLET IMAGING RADIOLOGY, LLC, Salt Lake City, UT (US)

( * ) Notice: Subject to any disclaimer, the term of this patent is extended or adjusted under 35 U.S.C. 154(b) by 0 days.

(21) Appl. No.: 16/889,556

(22) Filed: Jun. 1, 2020

(65) Prior Publication Data

US 2020/0359982 A1    Nov. 19, 2020

Related U.S. Application Data

(63) Continuation of application No. 15/524,044, filed as application No. PCT/US2015/059530 on Nov. 6, 2015, now Pat. No. 10,667,777.

(60) Provisional application No. 62/076,340, filed on Nov. 6, 2014.

(51) Int. Cl.
*A61B 6/00* (2006.01)
*G01N 23/04* (2018.01)
*G21K 7/00* (2006.01)

(52) U.S. Cl.
CPC .......... *A61B 6/505* (2013.01); *A61B 6/4283* (2013.01); *A61B 6/461* (2013.01); *A61B 6/508* (2013.01); *A61B 6/563* (2013.01); *A61B 6/582* (2013.01); *G01N 23/04* (2013.01); *G01N 2223/633* (2013.01); *G21K 7/00* (2013.01)

(58) Field of Classification Search
CPC ....... A61B 6/4283; A61B 6/461; A61B 6/505; A61B 6/508; A61B 6/563; A61B 6/582; G01N 2223/633; G01N 23/04; G21K 7/00
See application file for complete search history.

(56) References Cited

U.S. PATENT DOCUMENTS

| | | | |
|---|---|---|---|
| 4,721,112 A * | 1/1988 | Hirano | G06T 7/00 378/53 |
| 5,142,559 A * | 8/1992 | Wielopolski | A61B 6/08 250/492.3 |
| 6,422,750 B1 * | 7/2002 | Kwasnick | A61B 6/06 378/154 |
| 10,667,777 B2 * | 6/2020 | Echols | A61B 6/4283 |
| 2007/0172025 A1 * | 7/2007 | Seto | A61B 6/583 378/18 |

(Continued)

*Primary Examiner* — Chih-Cheng Kao
(74) *Attorney, Agent, or Firm* — Steptoe & Johnson LLP; Robert Greenfeld

(57) ABSTRACT

A system for radiographic tissue density evaluation includes a cassette for exposure to an X-ray source, where the cassette is configured to obtain information to perform intensity standardization of a captured radiographic image of a subject, a calibration bar with a predetermined radiographic signature on or within the cassette to serve as reference for performing the intensity standardization, and a software program to perform analysis on and to provide a display of the captured radiographic image. The cassette also includes a radio-opaque backing with a spatial homogenous X-ray radiographic signature used to estimate a source-detector geometrical inhomogeneity.

7 Claims, 3 Drawing Sheets

(56) References Cited

U.S. PATENT DOCUMENTS

| | | | |
|---|---|---|---|
| 2011/0282181 A1* | 11/2011 | Wang | A61B 6/4007 600/407 |
| 2014/0016852 A1* | 1/2014 | Soboleski | G06T 5/007 382/132 |
| 2016/0000394 A1* | 1/2016 | Yoshikawa | A61B 6/505 378/56 |

* cited by examiner

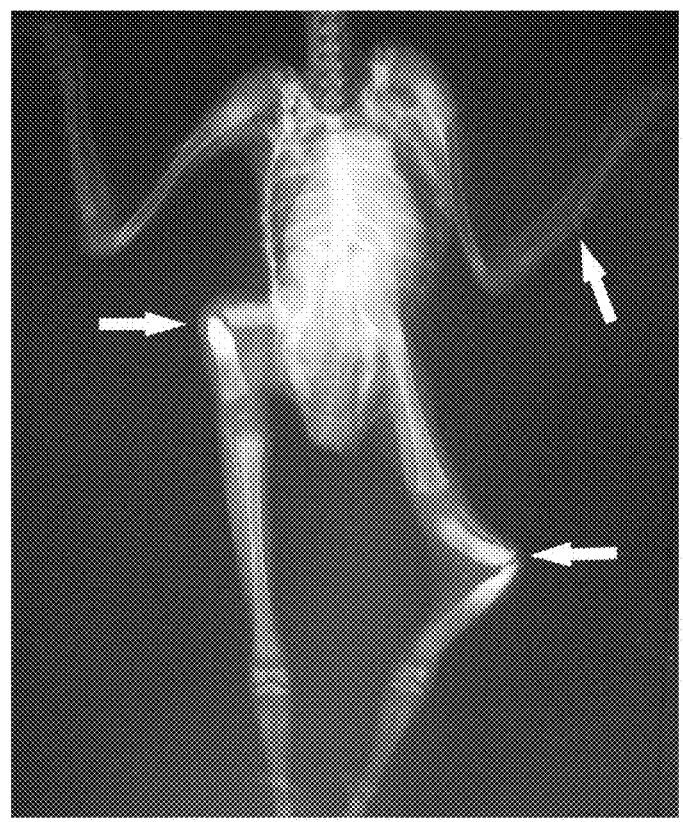
FIG. 1
(Prior Art)
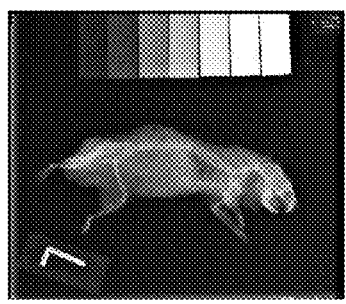
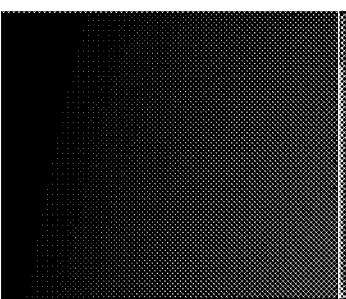
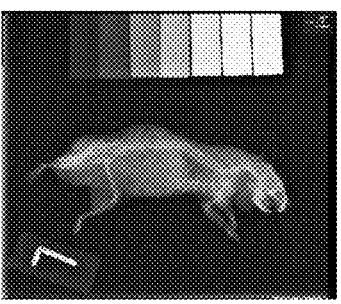
FIG. 2A      FIG. 2B      FIG. 2C

RADIOGRAPH DENSITY DETECTION DEVICE

CROSS-REFERENCE TO RELATED APPLICATIONS

This application is a continuation of U.S. application Ser. No. 15/524,044, filed May 3, 2017, now U.S. Pat. No. 10,667,777, which is a National Stage Application of International Application No. PCT/US2015/059530, filed Nov. 6, 2015. This application claims priority from U.S. application Ser. No. 15/524,044, International Application No. PCT/US2015/059530, and U.S. Provisional Patent Application Ser. No. 62/076,340, filed Nov. 6, 2014. Each of these applications is hereby incorporated by reference in its entirety.

FIELD OF THE INVENTION

The present invention in general relates to the field of imaging and in particular to an improved system and method for providing X-ray radiographs with quantitative and standardized levels for bone and other tissue density evaluations.

BACKGROUND OF THE INVENTION

Bone density is an important measure of bone health, and in some cases, systemic health of a subject. Low bone density has been identified as a risk factor for fractures (especially long, spinal vertebrae and pelvic bones), degenerative joint disease (arthritis), pain, decreased activity levels, certain disease states (bone cancers, select endocrine diseases, obesity, etc.), medications that result in bone loss, dental disease (due in part to loosened teeth) and even as a measure of welfare. Bone density disorders are recognized in both humans and non-human animals. By identifying poor bone density, clinicians have the opportunity to recognize and diagnose certain diseases earlier (as opposed to waiting for more overt disease to develop) and develop risk assessment protocols and hopefully preventative measures.

In addition, other tissue densities may also show promise for disease identification and serve as prognostic markers of certain diseases. This includes identifying the density of foreign materials that may have an impact on health. For example, by quantifying the density of ingested metals clinicians may be able to determine if conservative therapy results in successful dissolution of the item (by measuring decreasing density over a set period of time). Additionally, non-bone tissues that are more or less radiodense than "normal" may indicate a disease process is present. As an example, hyperadrenocorticism, certain kidney disorders and select toxins can increase mineralization in soft tissues.

Furthermore, low bone density also correlates with poor diet, lack of exercise, and lack of natural light exposure (especially for diurnal species), and may be compared to "normal" to better determine welfare of animals kept in captivity. The ultimate goal would be to improve conditions for captive animals by improving nutrition, activity level and natural UV light exposure, especially for those animals that have restricted access to natural light, sufficient room to ambulate, and/or are on a poor diet. Bone density has been studied in laboratory animals and in poultry species, where low bone density has been found to be a common problem in captive production birds. Advanced cases may easily be recognized by strikingly poor bone density and sometimes folding type fractures on standard radiographs, as shown in the example in FIG. 1. However, studies in other animals are critically lacking primarily due to the cost of diagnostic equipment. As a result, large scale studies that correlate bone/tissue density with health and disease states are not possible without substantial funding.

Advances in medical imaging technology have allowed noninvasive visualization and measurements of a wide variety of anatomy and functions of the body. Radiodensity or radiopacity refers to the relative inability of electromagnetic radiation, particularly X-rays, to pass through a particular material. Radiolucency indicates greater transparency or "transradiancy" to X-ray photons. Materials that inhibit the passage of electromagnetic radiation are called radiodense, while those that allow radiation to pass more freely are referred to as radiolucent. The term refers to the relatively opaque white appearance of dense materials or substances on radiographic imaging studies, compared with the relatively darker appearance of less dense materials. Because calcified tissues such as bone are radio-opaque, X-ray based imaging including projection radiography (or X-ray radiography) and computed tomography (CT) are the most commonly used modalities for assessing bone morphology.

Although X-ray radiography offers the highest spatial resolution useful for detecting, for example, hairline fracture in a bone, due to the lack of calibration and the physics of image formation, X-ray radiography intensities are generally only qualitative in nature. Due to its qualitative nature, X-ray radiographs give clinicians only subjective, relative evaluation of tissue density. As a result, standard radiographs, which are common in private practice, cannot be used to provide scientifically meaningful data on bone/tissue density. In contrast, CT intensities are both quantitative and standardized across all scanners, and are the best (in terms of speed and resolution) for visualizing the skeletal system and some soft tissue structures.

There are several reasons why existing X-ray radiography is not suited for quantitative intensity-based evaluations. Most X-ray radiography and CT instruments employ a "point source" for generating the X-ray. As the generated X-ray radiates away from the source, the intensity of the X-ray decreases as the inverse-square of the distance. Moreover, as the X-ray arrives at the detector, which is normally flat, unless the incident angle is perpendicular to the detector, the intensity of the X-ray is further diminished as the X-ray beam is spread across a bigger area. Combined, even when the point source is aimed directly and squarely at the detector, the "source-detector geometry" imposes an inherent variability on X-ray intensity across the detector. Whether a conventional film or digital detector is used, spontaneous processes in the detector (e.g., intrinsic electronic charges in the digital detector) contributes to baseline intensity in the X-ray image even when the source is completely turned off. Due to the properties of exposure-to-intensity conversion, the conversion might not be linear (i.e., doubling the exposure may not result in doubled brightness on the image). In addition to the baseline and nonlinear responses, all detectors have finite response "dynamic range." Unless the exposure is optimized to the range, under-exposure can lead to patches of uniformly dense regions (regardless of variability of the underlying anatomy), whereas over-exposure can lead to apparent disappearance of low-density regions.

In computed tomography (CT), all of the above issues with X-ray radiography are effectively addressed by the so-called "dark-light calibration" and "exposure optimization" procedures that are performed as part of the CT acquisition. The dark-light calibration essentially involves obtaining scans with and without the source turned on, and subtracts the obtained values from all subsequent acquisitions. Exposure optimization involves an iterative process of scans and intensity analysis to find the exposure setting that is just below the upper detector dynamic range. Separately, all CT-obtained intensities are standardized by normalizing the intensities to those for air and water, such that air and water will have exactly 1000 and 0 "Hounsfield Units," respectively, in all scanners.

Even though CT provides the best speed and resolution for visualizing the skeletal system, the cost of CT scans is prohibitive and the limited availability of CT equipment makes its wide usage impractical in most veterinary and human point-of-care practices. Thus, there exists a need for improved systems and methods that provide skeletal visualizations that are comparable to CT scans but at a lower cost and with lower dosimetry.

SUMMARY OF THE INVENTION

A method for radiographic tissue density evaluation is provided that includes capturing a radiographic image of a material with an X-ray image collection cassette. The cassette includes components (either built in or attached to the cassette) that allow for performing intensity standardization of the captured radiographic image. A spatial homogenous backing alone, at least one calibration bar, or a combination thereof serve as a reference for such standardization through background subtraction and known absorption, respectively. The radiographic image is analyzed to determine spatially resolved tissue/subject density in the biological or non-biologic material. The biological material can be a biopsy, a microorganism, an organ, organelle, or a living subject such as a human or an animal, or a cadaver. The non-biologic subject can be any device, structure or other item not composed of biologic material. A system for performing the method is also provided that includes a standard or specialized X-ray image recordation cassette and software for radiographic image analysis.

BRIEF DESCRIPTION OF THE DRAWINGS

The present invention is further detailed with respect to the following drawings. These figures are not intended to limit the scope of the present invention but rather illustrate certain attributes thereof.

FIG. 1 is a prior art radiograph of a juvenile barn owl (*Tyto alba*) with severe metabolic bone disease and multiple folding fractures (arrows);

FIGS. 2A-2C are an as taken a radiograph of an ex vivo hamster (FIG. 2A) with an intensity calibration bar (top of image) according to an embodiment of the invention, background isolation (FIG. 2B) and the image of FIG. 2A after subtraction of the background of FIG. 2B (FIG. 2C);

DESCRIPTION OF THE INVENTION

Figure 3A:
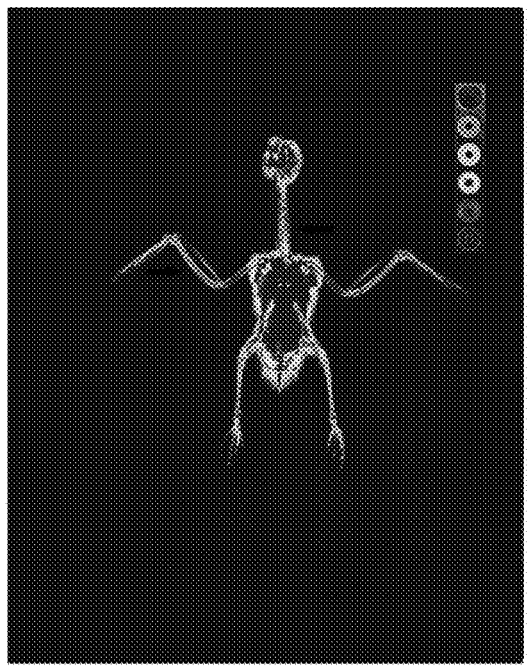
FIGS. 3A-3D are color density maps of two cockatiels according to the present invention, with FIGS. 3A-3B representing images for the first cockatiel, and FIGS. 3C-3D representing images for the second cockatiel.

The present invention has utility as a method and system to make X-ray radiographs sufficiently quantitative and standardized for bone, other tissue and non-biologic subject density evaluations. Embodiments of the inventive X-ray radiograph methodology and system provide a cost effective diagnostic tool that may be used in daily practice with existing X-ray radiography equipment already present in many clinics and hospitals to ultimately produce large volumes of scientifically valid data and useful diagnostic and prognostic information.

Embodiments of the inventive radiograph based bone, tissue, non-biologic subject density determination system are designed to visually and numerically identify bone and other densities using digital radiographs. The values generated are based on a universal scale, different from Hounsfield units, that can be standardized from radiograph to radiograph and across machines assuming proper radiograph positioning and technique (for the subject in question) is used and radiographic equipment is functioning properly. The inventive system may be used as a low cost alternative to more expensive density imaging methods such as computerized tomography (CT) and Dual-energy X-ray absorptiometry (or DEXA) scans.

Embodiments of the invention may be used in any situation where radiographs are taken—standard limb or whole body images, dental, clinical patient, research—and on potentially any animal including humans. Embodiments of the inventive X-ray radiograph methodology and system may also potentially be used on plants, minerals, metals, manmade materials and any other naturally occurring or foreign substance, industrial equipment, and other objects and structures, serving as an inexpensive way of collecting density information, with radiation dosing that is less than that of CT scanning. Materials suitable for density interrogation according to the present invention illustratively include a whole multicellular organism, a microbe, a virus, or parts of an organism (as in a specific organ, organelle, or tissue), or non-biological materials such as castings. The applications include obvious health data, but could be used as a screening tool for density variations in just about any material or object. A living human or animal or cadaver of the same are exemplary materials in a clinical setting.

To form the inventive Radiograph Density Detection Device (RDDD) (hereinafter referred to as a radiographic device, or simply the device) a component may be added to a conventional X-ray film cassette (internally as a part of the cassette or peripherally attached to the cassette) and subsequently incorporated into radiographs for interpretation. The incorporated device acts as a standard against which animal, human, non-biological, and other tissue densities can be measured. An inventive software based program is provided to interpret tissue densities (including bone) to ultimately identify low, normal, or high values compared to "normal" densities. Densities created by the software may be presented in a variety of forms illustratively including density associated colors and absolute numerical values and can give local regional and whole subject values. In some inventive embodiments, orthogonal views of the same material can be used to by the software to mathematically generate volumetric color and numerical values for the material. The inventive device provides the diagnostician real data as to the density of normal and foreign body tissues to aid in disease diagnosis and prediction of health of a subject either human or animal. Non-biologic material densities can also be rapidly studied as with biologic materials to, for example, identify internal porosity or voids in a casting.

Embodiments of the inventive device and method provide a low cost and relatively accurate (within an acceptable tolerance or error) alternative to CT or other more expensive and generally unavailable diagnostic tests that evaluate bone and other tissue densities in patients, with generally lower radiation exposure. Embodiments of the device may be used on digital radiograph machines which are now commonplace in human and animal medical facilities with embodiments of the inventive software to convert the images obtained into tissue density scores. Embodiments of the invention require minimal modification or additional procedure to the effort involved in taking a conventional X-ray radiography. It is appreciated that an X-ray microscope is also used to obtain density information regarding materials smaller than a few millimeters.

The following are non-limiting illustrative examples of specific types of disorders where evaluation using the above RDDD system may improve diagnosis and potentially treatment:

Soft tissues: muscle contraction; myositis ossificans; vascular diseases (mineralization, atherosclerosis); tenosynovitis; tendon avulsion; inflammation (traumatic, parasitic, fungal, bacterial, neoplastic, autoimmune, toxins, thermal burns, freezing injury, idiopathic, nosocomial, exogenous drug induced, endogenous drug induced, etc.); general abnormal mineralization or mineral deposits; tissue disruption; duplicate, hypertrophied, atrophied, missing, reversed or misplaced organs/tissues; foreign bodies, granulomas, calculi formation, calcinosis cutis; panniculitis; intervertebral disk disease; periodontal disease; joint/tendon/ligament ruptures; retained cartilage cores; fibrotic myopathy; and general and organ specific neoplasia. Diagnosis of any disorder that alters the density of soft tissues may potentially benefit from the RDDD.

Bone tissues: osteomalacia; osteoporosis; osteodystrophy; osteomyelitis (traumatic, parasitic, fungal, bacterial, neoplastic, autoimmune, toxins, thermal burns, freezing injury, idiopathic, nosocomial, exogenous drug induced, endogenous drug induced, etc.); panosteitis; vitamin A toxicity; periosteal inflammation (traumatic, parasitic, fungal, bacterial, neoplastic, autoimmune, toxins, thermal burns, freezing injury, idiopathic, nosocomial, exogenous drug induced, endogenous drug induced, etc.); osteoarthritis/degenerative joint disease; rheumatoid arthritis; erosive arthritis (single or poly); non-erosive arthritis (single or poly) (traumatic, parasitic, fungal, bacterial, neoplastic, autoimmune, toxins, thermal burns, freezing injury, idiopathic, nosocomial, exogenous drug induced, endogenous drug induced, etc.) osteitis (traumatic, parasitic, fungal, bacterial, neoplastic, autoimmune, toxins, thermal burns, freezing injury, idiopathic, nosocomial, exogenous drug induced, endogenous drug induced, etc.); periosteal bruising; fractures; multiple cartilaginous exostoses; diskospondylitis; Legg-Calvé-Perthes disease; osteochondrosis; septic arthritis (traumatic, parasitic, fungal, bacterial, neoplastic, autoimmune, toxins, thermal burns, freezing injury, idiopathic, nosocomial, exogenous drug induced, endogenous drug induced, etc.); craniomandibular osteopathy; bone cysts; hypertrophic osteopathy; nutritional secondary hyperparathyroidism; renal secondary hyperparathyroidism; mucopolysaccharidosis; bone mutilation from injury, infection, self-trauma, other; monitor bone biopsy and graft/implant sites, and more. Diagnosis of any disorder that alters the density of bone may potentially benefit from the RDDD.

Figure 4A:
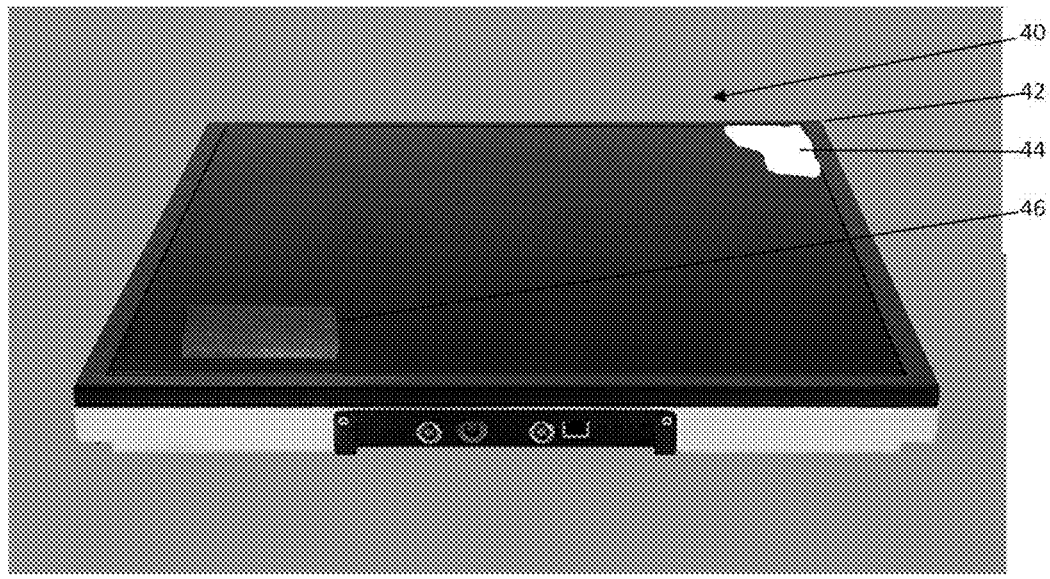
FIGS. 4A-4B are schematics of a cassette showing a backing and calibration bar in two different inventive embodiments.
Figure 4B:
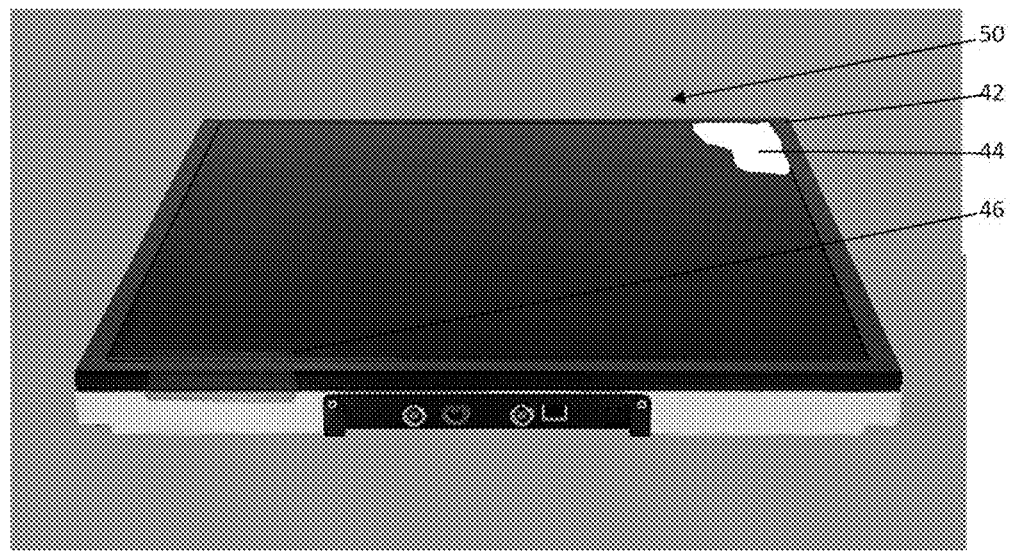

With respect to FIGS. 4A and 4B, in which like numerals have like meaning when ascribed to different drawings, a specific embodiment of the inventive device 40 or 50 in the form of a flat-bed cassette 42 is configured for placement under a human subject or other material as part of the regular X-ray radiography exam, in order to make X-ray radiography more quantitative and standardized. The cassette 42 captures information to perform intensity normalization and standardization, at locations (e.g., field hospitals) where care is rendered. The cassette may have (a) a minimally radio-opaque backing 44 which may be made of acrylic polymer or other radiolucent material or an image receptive layer that directly converts X-ray information into a digital signal, of uniform thickness whose X-ray radiographic signature can be used to estimate the source-detector geometrical inhomogeneity, and (b) a calibration bar 46 consisting of known materials and known thickness whose radiographic signatures can serve as references for standardization. In inventive embodiments the calibration bar acting as the reference device may fit on top of or within a radiograph cassette that is composed of a set of standard density items. In order to accommodate the wide range of X-ray exposures that may be encountered in the field, separate sets of the inventive cassette may be configured for use with low, medium and high exposures in part based on the size the subject.

The standard X-ray cassette 42 is utilized. The cassette 42 may be square, rectangular or specially shaped and sized for the subject. A calibration bar 46, composed of multiple materials of known density and proper size to account for changes in the X-ray direct and incident angles and cassette and subject sizes, may be built into the cassette 42, simply placed on top of the cassette 42 or interchangeably inserted into the cassette 42. Specially designed cassettes would house the interchangeable port or permanent location of the calibration bar. It is appreciated that a novel cassette is developed in which the entire cassette serves as the calibration bar such that additional components are not required.

The terms "low," "medium," and "high" are in the context of X-ray exposure for a given X-ray source. It is appreciated that the thickness and radio-density of the material being investigated are important aspects in deciding the exposure. Additionally, X-ray cassettes may have built-in calibration bars or similar devices that cover a larger range than afforded by individual and interchangeable bars.

The calibration bar on embodiments of the cassette is configured to have a sufficiently wide range and graduated radio-opacity (set of standard density items) for the entire dynamic range of exposure encountered in practice. This reference range provides densities which are compared to the subject's different tissues. In embodiments, software is configured to quickly interpret the information and provide real time data as to the densities of set and user defined points (a portion of a bone for example) as well as set and user defined regions (a whole bone for example).

Embodiments of the inventive software are configured to perform numerical operations to convert raw X-ray radiographic intensity into standardized metrics to be used in, for example, evaluating bone density. The software may be installed on a server or computer that is located in the same hospital or location where the scans are performed, or the software may be on a remote server or offered as a software on-demand service in the cloud that is accessed over the Internet. The images may be transmitted to a central location to be processed and analyzed by the same persons, although the software for the analysis can also be distributed to the field locations. The inventive software includes capabilities to (a) estimate the background (created by the instrument source-detector geometry and baseline responses) and subtract it from the raw image, and (b) convert the grayscale images into color-coded images (an intuitive colormap) based on the reference materials, since the human eye can more readily discern different colors over different shades of grey. In a specific embodiment, the colormap scale follows the visible spectrum with normalized radiodensity values from 0-100 corresponding to a color progression from red to violet, or vice versa.

Because of the inherent variation in background intensity generated in X-ray radiography (in part due to the physics of x-rays diverging from the perfect perpendicular orientation of the central ray and the receptor plate), another embodiment of the inventive software is to adjust for this variation and create a homogeneous background on the image. FIGS. 2A-C demonstrate the gradient naturally present in X-ray images. Without correction, this gradient affects the visual brightness of images and ultimately results in variation, of what may be the exact same density, from one side of the film to the other. The inventive software corrects for this gradient across the X-ray image creating density values consistent with the true density of the subject. In another embodiment of the inventive software enhancement tools added to the image, by the native digital image processing software, are accounted for and counteracted, minimized or otherwise adjusted for to reduce their effect on further density processing. Such digital imaging tools, such as sharpening type tools, are common with digital imaging software. These tools are designed to help the viewer discern subtleties in the greyscale of the image. Sharpening and shadowing can help define lines in between various grey scales and are often used to help the image visually "pop." However, these shadows, sharpenings and other changes can artificially affect the density of certain subject attributes and must be considered. The inventive software also works to address some or all of these enhancement tools that may be present—especially those that may affect density readings. Correction may include working with the manufacturer of the native software to turn off these features or by adjusting for the changes created from the enhancement tool(s).

The ability of the inventive software to convert the grayscale images into color-coded images allows for creation of density color maps that may be adjusted through a series of density ranges. This allows the image to be intensified (amplify the density signal) for specific regions as needed. The adjustable intensity range may be applied to any image and directly compared between images of different subjects. Embodiments of the inventive software generate real values that correspond to the density range (whether amplified or not), which assigns a "number" on the density value that can also be compared with the subject and between subjects.

Specific embodiments of software algorithms used for image correction create a correction methodology that will produce quantitative values of radio-opacity in X-ray radiography that are within 5-15% accuracy of the values measured by CT. In a preferred embodiment radiographic density information is within 95%, or greater, correlation of CT density values (Hounsfield units). The radiographic density score is consistent between any X-ray machine using the inventive flat-bed cassette and only requires proper patient/subject positioning and the use of the inventive operating software. The user would simply click a "button" and get a color coded density map for an overview of density, regional, and even localized views. Real "density" values may be collected regionally, locally, and even in very specific spots/pixels on a subject. These density values may be used to identify variations from "normal" or expected values.

In inventive embodiments identified combinations of materials and thicknesses that have discrete, gradated radio-opacity suitable for the construction of a radio-opacity calibration bar are formed. The identification of material includes the backing board and/or its thickness in order to accommodate the X-ray exposures that will be used for different-sized animals and subjects.

EXAMPLES

Example 1

FIGS. 2A-2C show a radiograph of an ex vivo hamster (FIG. 2A) with an embodiment of the intensity calibration bar (top of image). In the radiograph of FIG. 2A, there is a conspicuous background that increases in intensity (dark to light) from left to right of the image. The non-uniform background is isolated (FIG. 2B), which contributes to approximately 10-15% of the intensity variation across the image in this specific example. After subtracting the background, the corrected image (FIG. 2C) shows visibly improved contrast and detail, especially in the animal head. Importantly, the intensities can now be assigned bone density values with more certainty by cross-referencing with the calibration bar.

Example 2

Validation of embodiments of hardware-software methodology in making X-ray radiography quantitative is obtained with radiographs of different objects as well as ex vivo animals of varying sizes, and performing post-analysis corrections, and compare the corrected radiographs directly with CTs of the identical objects and animals. The results may be used as feedback for improving the software algorithms of the correction.

Example 3

Figure 3B:
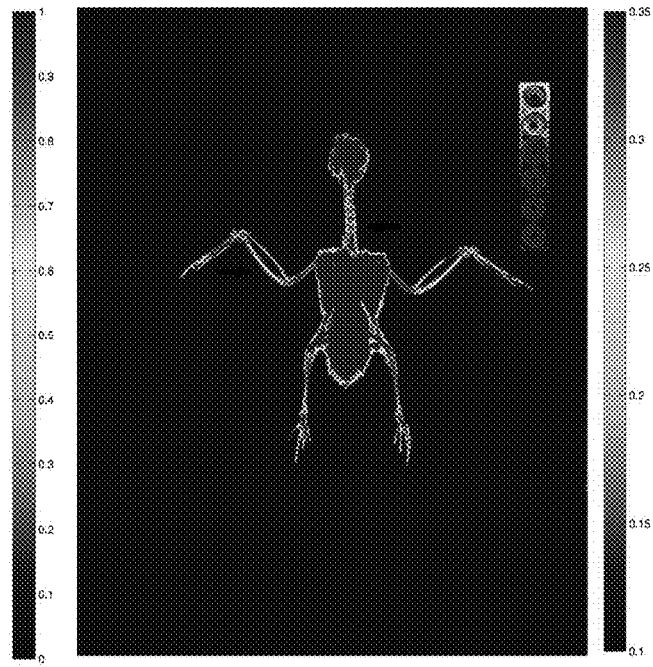
Figure 3C:
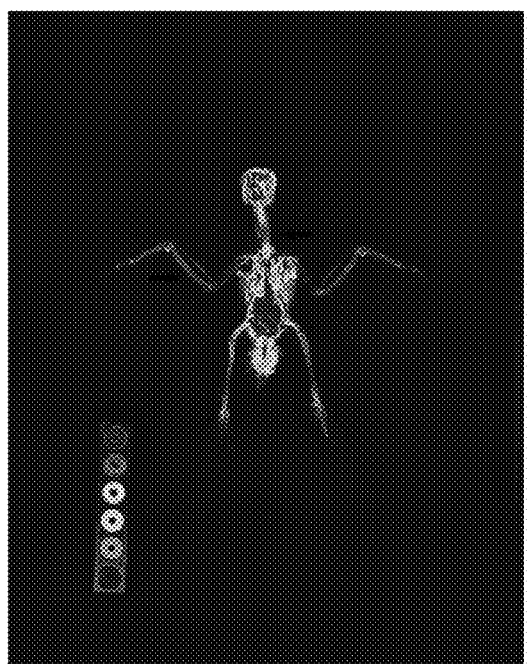
Figure 3D:
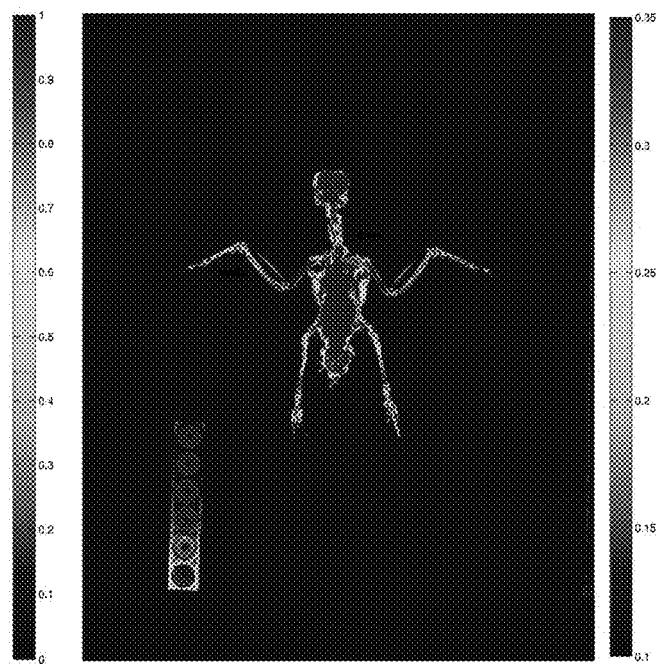

FIGS. 3A-3D are corrected radiographs (X-ray image) with color density maps of two cockatiels. FIGS. 3A and 3B refer to cockatiel 1, and FIGS. 3C and 3D refer to cockatiel 2. The animals are approximately the same size and radiographs were completed on the same machine with identical settings. FIGS. 3A through 3D show the calibration bar (represented by circles of varying colors and, subsequently, densities). The birds were first radiographed with a standardized calibration bar creating unprocessed images. Next the same images underwent post-processing to even the background gradient. The second step ensures that all, or at least most, points on the image have been adjusted for the gradient variation and is crucial to the next step of assigning density values to the tissues. FIGS. 3A and 3C show cockatiel 1 and cockatiel 2, respectively, with a color map and identical density scale (right side of image). Each color corresponds to a density value that can also be represented with a numerical value. The reddish-brown color indicates the greatest density while blue indicates the lowest density. Both subjects can be compared directly. The black arrows point to regions that are brighter in FIG. 3A compared to 3C. The density scale can also be narrowed which makes the density readings more sensitive for those areas with decreased density. FIGS. 3B and 3D demonstrate a narrowed density scale that increases subtleties in the images. Again, both subjects are shown at identical density scales. The arrows are placed to allow for direct comparison of color based densities between the two subjects. The arrows point to greater density readings (as shown with increased reddish-brown and yellow) in FIG. 3B compared to the same regions on FIG. 3D (more white and blue representing lower density). In this example, bird 1 (represented by FIGS.

3A-3B) has much greater bone density than the bird represented by FIGS. 3C-3D. However, this difference is not readily observable in plain radiographs. The color scheme is directly tied to numeric values and can be compared between subjects and machines. The color representation allows for quick assessment of density. Even if the scale (and corresponding colors) is changed, the numeric values are consistently reported (as long as the area being measured is not over or undersaturated). The numeric values allow for reporting that can be compared to "normals" and "abnormals" without the risk of over or under interpreting the color map.

Example 4

A validation study of hardware-software methodology is conducted to test how well it performs under various conditions of normal usage on different X-ray equipment. To provide a basis for comparison, "phantoms" (objects for test scans) are constructed that correspond to large, medium and small-size animals or human tissues. CT scans are performed on the phantoms to obtain absolute quantification of their radio-opacity values. Moreover, 4 duplicate sets of the backing boards, calibration bars, and phantoms are sent to 10-24 selected veterinary clinics around the country for trial scans on different equipment. The scans obtained from different sites are compared and the results may be used to improve the robustness of the post-analysis algorithm with a goal is to obtain quantitative X-ray radiograph values that are consistent within 5% across different scanners at different sites. Additional veterinary and human hospitals and other testing centers may be recruited to aid in product improvement.

Example 5

A study of 4 sets of birds (2 species, each under 2 sets of conditions) using the inventive Radiograph Density Detection Device (RDDD) and a micro computerized tomography ($\mu$CT). The $\mu$CT will serve as the gold standard. Data is collected on all birds at two separate times.

The study is designed to accomplish two goals: correlate the RDDD to $\mu$CT and collect bone density readings between the different groups of birds. As a tertiary goal, the study serves as a model of how the RDDD can be used on a large scale basis.

Data points collected are used to form a best fit model on the radiographs compared to $\mu$CT, to determine how reliable the RDDD data is at specific points on the radiographs and to provide a correlation coefficient with $\mu$CT.

Example 6

Clinical use of the Radiograph Density Detection Device (RDDD) to develop normal and abnormal density ranges for specific tissues/items, study individuals/single items and populations/groups.

The test may be used as a typical component of X-ray testing whether for screening, diagnostic or monitoring purposes.

The development of normal and abnormal density ranges may be used as a diagnostic tool and as a long term ongoing means to develop and refine what normal density is for the specific subject being studied. For example, the RDDD may be used to collect data on bone density values for a population of people living in a certain local. In an alternative example, the RDDD could be used to monitor environmental degradation of select minerals or metals after exposure to acids and other contaminants.

Example 7

Studies may be based on data gathered using the RDDD system. The data generated by embodiments of the RDDD system could provide a large amount of information relating to individuals (such as people), populations (such as captive animals), construction materials (as with weathering and mineral leaching of materials) and more. Examples of such studies in humans and animals include but are not limited to relating bone density to inactivity; obesity; cage or space confinement; subzero, zero or increased gravity; nutrition; whole organism or organ specific development, and much more.

The foregoing description is illustrative of particular embodiments of the invention, but is not meant to be a limitation upon the practice thereof. The following claims, including all equivalents thereof, are intended to define the scope of the invention.

The invention claimed is:

1. A system for radiographic tissue density evaluation, said system comprising:
  a cassette configured to be exposed to an X-ray source and configured to obtain information to perform intensity standardization of a captured radiographic image of a subject, the cassette having a minimally radio-opaque backing with a spatial homogeneous X-ray radiographic signature used to estimate a source-detector geometrical inhomogeneity;
  a calibration bar with a predetermined radiographic signature on or within the cassette to serve as reference for performing the intensity standardization; and
  a software program to analyze and display the captured radiographic image.

2. The system of claim 1, wherein the minimally radio-opaque backing is made of acrylic polymer or other radio-lucent material, having a uniform thickness.

3. The system of claim 1, wherein the calibration bar further comprises a graduated radio-opacity inset of standard density items to form a reference range for an entire dynamic range of X-ray exposure.

4. The system of claim 1, wherein the display further comprises a color-coded intensity image that forms an intuitive colormap based on the calibration bar.

5. The system of claim 1, wherein the software program is installed on a server or a computer that is located in the location of the X-ray radiography machine.

6. The system of claim 1, wherein the software program is installed on a remote server accessed over the Internet.

7. The system of claim 1, wherein the software program is offered as a software on-demand service in the cloud that is accessed over the Internet.

* * * * *